United States Patent [19]

Yuen et al.

[11] Patent Number: 4,645,635
[45] Date of Patent: Feb. 24, 1987

[54] METHOD AND APPARATUS FOR DETERMINING THE PROPERTIES OF WET STEAM

[75] Inventors: Peter S. L. Yuen; Philip Campbell; John L. Montin; Keith H. Ardron, all of Pinawa, Canada

[73] Assignee: Atomic Energy of Canada Limited/l'Energie Atomique du Canada LTEE, Ottawa, Canada

[21] Appl. No.: 697,401

[22] Filed: Feb. 1, 1985

[30] Foreign Application Priority Data

Sep. 6, 1984 [CA] Canada .................................. 462592

[51] Int. Cl.$^4$ .............................................. G21C 17/00
[52] U.S. Cl. ..................................... 376/245; 376/159; 250/390; 374/42
[58] Field of Search ..................... 376/110, 159, 245; 250/390, 391, 392; 374/141, 42

[56] References Cited

U.S. PATENT DOCUMENTS

| | | | |
|---|---|---|---|
| 3,299,268 | 1/1967 | Muto et al. | 376/159 |
| 3,496,357 | 2/1970 | Weinzierl et al. | 376/159 |
| 4,200,789 | 4/1980 | Arnold et al. | 376/159 |
| 4,263,098 | 4/1981 | Tasperek et al. | 376/159 |
| 4,266,132 | 5/1981 | Marshall, III | 250/390 C |
| 4,362,939 | 12/1982 | Horiuchi et al. | 250/390 D |
| 4,499,380 | 2/1985 | Aggour et al. | 250/390 C |

Primary Examiner—Daniel M. Yasich
Attorney, Agent, or Firm—Yoshiharu Toyooka

[57] ABSTRACT

A partially collimated beam of thermal/epithermal neutrons is transmitted through a small bore pipe in which wet steam flows under a high pressure. A thermal neutron detector measures the transmission of the thermal/epithermal neutrons by the wet steam and generates a signal indicative of the density and steam quality of the wet steam.

17 Claims, 6 Drawing Figures

METHOD AND APPARATUS FOR DETERMINING THE PROPERTIES OF WET STEAM

This invention relates to measuring properties of steam and, more specifically, is concerned with applications of thermal/epithermal neutron beams for measuring such properties as the density and quality of high pressure wet steam in small pipes.

BACKGROUND OF THE INVENTION

The density measurement of high pressure wet steam in small pipes is needed in many industrial processes. One example is in crude oil extraction where high pressure, wet steam injection is sometimes used for cracking underground formations of heavy crude oil. In this application, it is desirable to monitor the density of wet steam so that the corresponding quality of steam is maintained within desired limits. These limits on the density of wet steam are usually set such that the quality of steam is high enough to crack and soften the crude formation and yet wet enough to remove depository particles from the boiler. Another example is found in the electric power industry where steam produced from a steam generator is used to drive a turbine producing electricity. In this case, it is very important to measure the density in order to ensure that the density is below the allowed limit so that the turbine functions properly.

There have been, in the past, various proposed methods of measuring the density of a steam-water mixture and they use, (a) quick closing valves, (b) impedance probes, (c) optical probes, and (d) ultrasound probes. All these methods, however, possess one or more of the following shortcomings:

(a) the method is intrusive and disturbs the flow of steam,
(b) the method disturbs the routine operation of processes,
(c) the method is not applicable because of a thick steel pipe wall,
(d) the method is not sensitive, and/or
(e) the device is not portable.

Other methods of measuring the density of high pressure, wet steam use the attenuating/scattering characteristics of radiation which the wet steam possesses. The wet steam is defined as a steam-water mixture having a high void fraction. The void fraction is a volume fraction occupied by steam phase).

These methods operate on the attenuation/transmission of various radiations like X-rays, $\beta$ particles and $\gamma$-rays. However, X-rays and particles cannot penetrate thick metal pipe walls. Gamma rays can penetrate thick pipe walls but is very insensitive in the high void region (wet steam). The scattering of epithermal/fast neutrons has proven very sensitive in the low and intermediate void fraction region and in pipes of bigger diameter (D>50 mm). However, it becomes quite insensitive in the high void fraction region, particularly in small pipes because the probability of thermalization is small.

U.S. Pat. No. 4,243,886, Jan. 6, 1981, (Untermyer), discloses a technique for determining the hydrogen content of such materials as wood or concrete, or the quantity of water in the human lung. The technique uses a source of fast neutrons and a thermal neutron detector. The source and the detector are positioned on one side of an object whose neutron moderating or absorbing properties are being measured. The fast neutrons from the source are moderated or absorbed to generate thermal neutrons in passing through the object and the detector detects thermal neutrons emerging from the object. A standard neutron absorber is used to derive the difference between the object and the standard in the thermal neutron counts at the detector. The difference is an indication of the moderating or absorbing properties of the object.

In U.S. Pat. No. 3,350,564, Oct. 31, 1967, (Bonilla et al), a method of measuring the void fraction of boiling water using neutron attenuation is described. This patent uses small amounts of boron which are dissolved in the water to absorb the neutrons and a beam of low energy neutrons is transmitted through the boiling water. The amount of attenuation is related to the void fraction of the water.

OBJECTS OF THE PRESENT INVENTION

It is an object of the present invention to provide an apparatus for and a method of measuring properties of high pressure wet steam in a small pipe through the use of thermal/epithermal neutron transmission.

It is another object of the present invention to provide an apparatus for and a method of measuring the density of high pressure wet steam in a small pipe through the use of thermal/epithermal neutron transmission.

It is still another object of the present invention to provide an apparatus for and a method of measuring the steam quality of high pressure wet steam in a small pipe through the use of thermal/epithermal neutron transmission.

It is noted that throughout this specification and drawings, the term "thermal/epithermal neutron" means a neutron having the energy in the thermal or epithermal range. It is also understood that a thermal neutron detector is quite sensitive to the epithermal neutrons as well as thermal neutrons.

BRIEF DESCRIPTION OF THE INVENTION

Briefly stated, the present invention makes use of a partially collimated beam of thermal/epithermal neutrons which is transmitted through a metal pipe of a small bore containing high pressure wet steam. A thermal neutron detector detects the transmitted thermal/epithermal neutrons and generates a signal proportional to the thermal/epithermal neutron counting rates which is indicative of such properties of the wet steam as the density and steam quality.

Accordingly, the method of the present invention is for determining a property of high pressure wet steam in a metal pipe of a small cross-sectional area in which the said property is related to the transmission characteristic of thermal/epithermal neutrons through the high pressure wet steam. The method includes steps of generating neutrons of energies above thermal and epithermal range from a neutron source and moderating the neutrons from the neutron source to thermal/epithermal neutrons by means of the neutron moderating material. The method further includes steps of collimating the thermal/epithermal neutrons into a beam by means of a straight collimating extraction hole of a small cross section provided in the neutron moderating material, the said extraction hole extending from the exterior surface of the neutron moderating material to near the neutron source, transmitting the collimated beam of thermal/epithermal neutrons through a pipe and receiving by a thermal neutron detector, the thermal/epithermal neutrons transmitted through the pipe to generate an output proportional thereto. The method further includes a step of processing the output to produce an indication of the property of the high pressure wet steam, the said property being either the steam quality or the density.

The apparatus of the present invention is for determining a property of high pressure wet steam in a metal pipe of a small cross-sectional area in which the said property is related to the transmission characteristic of thermal/epithermal neutrons through the high pressure wet steam. The apparatus comprises a neutron beam extractor positioned near the exterior surface of the pipe to transmit a collimated beam of thermal/epithermal neutrons through the pipe. The neutron beam extractor has a radioactive neutron source to emit neutrons of energies above thermal and epithermal range and source support means made of a neutron moderating material. The said source support means further has a chamber formed therein in which the radioactive neutron source is positioned and a straight collimating extraction hole of a small cross section in the said neutron moderating material. The said extraction hole extends from the exterior surface of the source support means to near the chamber wherein the chamber and the extraction hole are spaced apart by a predetermined amount so that the fast neutrons emitted by the source will be moderated to become thermal/epithermal neutrons as they emerge into the extraction hole which will then collimate the thermal/epithermal neutrons into a beam. The apparatus further includes a thermal neutron detector, positioned near the exterior surface of the pipe on the side opposite to the neutron beam extractor, to receive the thermal/epithermal neutrons transmitted through the pipe and to generate an output proportional thereto. The apparatus further includes electronic counting means for generating, from the output of the thermal neutron detector, an indication of the transmitted thermal/epithermal neutron counting rate which in turn is an indication of the property of the high pressure wet steam.

The property that the method and the apparatus of the present invention determine can be, the density or the steam quality of the high pressure wet steam.

BRIEF DESCRIPTION OF THE DRAWINGS

For a more complete understanding of the present invention and for further objects and advantages thereof, references may now be made to the following description taken in conjunction with the accompanying drawings, in which.

DETAILED DESCRIPTION OF THE EMBODIMENTS

The counting rate of transmitted thermal/epithermal neutron through the pipe decrease fairly linearly with the density of the wet steam. Upon calibration against known wet steam density, the device can be used to measure the density of wet steam.

The density, $\rho$, of a steam-water mixture is related to void fraction $\alpha$ (volume fraction occupied by steam phase) by:

$$\rho = \rho_g \alpha + \rho_f(1 - \alpha) \quad (1)$$

where, $\rho$ = density of a steam-water mixture, $\rho_g$ = density of the steam phase, and, $\rho_f$ = density of the water phase.

Since $\rho_g$ and $\rho_f$ are state functions of pressure at saturation, measuring $\rho$ is equivalent to measuring void fraction $\alpha$.

Now the steam quality, x, is defined as the ratio of mass flow rate of the steam phase in the steam-water mixture to the total mass flow rate of the steam and water phases and is related to $\alpha$ by:

$$\alpha = \frac{1}{\left[1 + \frac{\rho_g}{\rho_f} \frac{U_g}{U_f} \frac{(1-x)}{x}\right]} \quad (2)$$

where $U_g$ and $U_f$ refer to the average velocities of the steam and water phase respectively. Thus, the transmitted thermal/epithermal neutron counting rate depends also on steam quality x. Therefore, it is possible to calculate the steam quality x by first measuring the transmitted thermal/epithermal neutron counting rate which is proportional to $\rho$ and then by using the above equations together with an appropriate value of $U_g/U_f$.

Or, the instrument can be calibrated against known steam qualities at a given pressure and flow rate, of a wet steam flow inside a pipe which is part of a flow loop, the geometry of which is identical to that in the intended field application. After calibration, the instrument can be used to measure steam qualities by using calibration curves.

Figure 1:
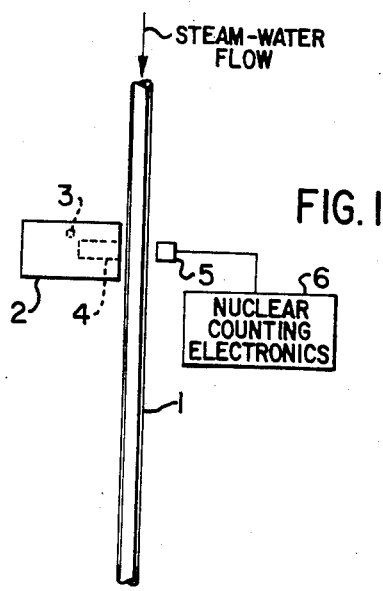
FIG. 1 is a schematic diagram showing a basic arrangement of the present invention.

Referring now to FIG. 1 of the drawings, wet steam flows in a metal pipe 1 under a relatively high pressure. The pipe is generally made of steel and has a relatively small bore, i.e. about 75 mm or less in diameter, in the case of a tubular pipe. A neutron beam extractor 2, positioned on one side of the pipe, has a collimator (or sometimes called extraction hole) 4 and a neutron source 3 of a radioactive isotope. A thermal neutron detector 5 is positioned on the opposite side of the pipe from the neutron beam extractor. The detector is primarily sensitive only to thermal and epithermal neutrons and detects thermal/epithermal neutrons emerging from the pipe after having undergone attenuation by the wet steam flow in the pipe. The output of the detector is led to an electronic counting means 6 where it is processed to generate a signal proportional to the counting rate of the transmitted thermal/epithermal neutrons, which is indicative of the density or quality of the high pressure wet steam. The electronic counting means is, for example, made up with a charge-sensitive pre-amplifier, a spectroscopic amplifier and a single channel analyzer to amplify and shape the detector output into pulses which are then counted over a fixed time span, and displayed. The number of transmitted neutrons counted over this fixed time span is dependent upon the density of the wet steam inside the pipe. The signal indicative of the density of the wet steam inside the pipe can be further processed by appropriate electronic circuits to generate an indication of the steam quality by using the equations (1) and (2) above. Or, the signal indicative of the density of the wet steam inside the pipe can be calibrated against known steam qualities of wet steam flow in a pipe which is part of a flow loop, the geometry of which is identical to that in the intended field application.

Figure 2:
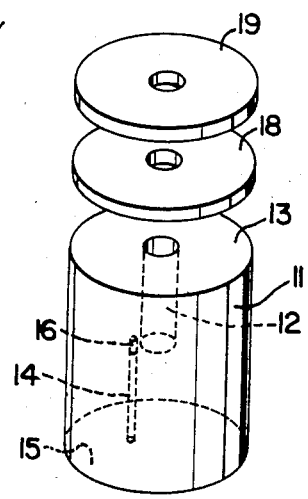
FIG. 2 is an exploded view of one embodiment of the neutron beam extractor according to the present invention.
Figure 3:
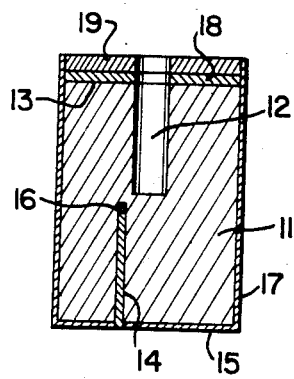
FIG. 3 is a sectional view of the neutron beam extractor shown in FIG. 2.

The neutron beam extractor is shown in more detail in FIGS. 2 and 3. In the figures, a sourc support 11 is shown of a generally cylindrical body of about 30 cm in diameter made of, for example, polyethylene containing light elements, such as hydrogen and carbon. Other shapes are also possible, such as spherical. A person skilled in the art would have no difficulty in choosing the right shape. The source support 11 has two blind cylindrical holes therein, the first hole 12 being of about 5 cm in diameter and extending straight from the first end 13 of the source support coaxially therewith, and the second hole 14 extending from the second end 15 of the source support. A neutron source 16, such as Cf-252, is placed in the second hole 14 at a position about 13 mm from the wall of, and about 13 mm from the bottom of the first hole. The neutron source 16 is attached at one end of a rod and is inserted into the second hole. The position of the source is adjustable along the second hole. The rod also closes the second hole when inserted. An aluminum layer 17, of about 2 mm thick, covers the second end and the cylindrical surface of the source support. An aluminum disk 18 covers the first end and has an opening coinciding with the opening of the first hole. Another disk 19 made of a suitable thermal insulator with an opening placed over the aluminum disk 18.

The neutrons of energies above the thermal and epithermal range emitted by the source 16 are moderated by the source support 11 made of polyethylene containing light elements, and many thermal/epithermal neutrons resulting from the moderation emerge from the first hole and are partially collimated. These extracted thermal/epithermal neutrons are transmitted through the wet steam in the pipe.

Figure 4:
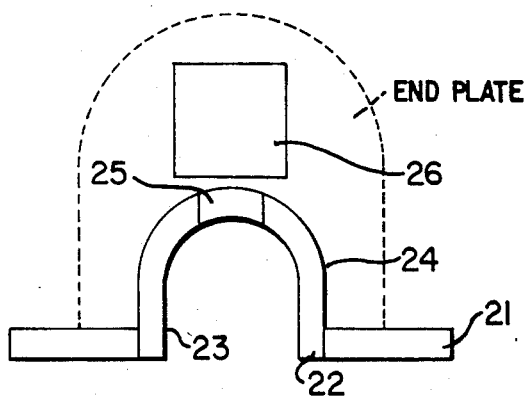
FIG. 4 is a brief sectional view of the neutron detector mount.

FIG. 4 shows one preferred embodiment of the thermal neutron detector mount. The mount has an aluminum base 21 on which a semicylindrical pipe seat is provided. The pipe seat is made by sandwiching a suitable thermal insulation 22 with an aluminum liner 23 and a cadmium sheath 24. The pipe seat has a hole 25 in it and a He detector 26 is positioned thereon to receive the thermal neutrons transmitted through the pipe and the wet steam contained therein.

Figure 5:
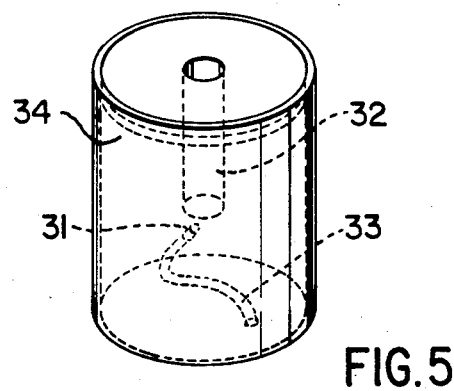
FIG. 5 shows another embodiment of the neutron beam extractor.

FIG. 5 shows another embodiment of the neutron beam extractor. In this embodiment, the neutron source 31 is located near the bottom of the extraction hole 32 and is on the axis thereof. This arrangement may increase noises at the detector caused by $\gamma$-rays and fast neutrons which many neutron sources also emit with varying degrees. Because the extraction hole 32 lies on the direct line of the $\gamma$-rays and fast neutrons, the detector counts more —rays and fast neutrons than it would in the embodiment of FIG. 2, where the source is offset with respect to the extraction hole. Different neutron sources can be chosen to compensate the increase. A person skilled in the art would have no difficulty choosing the right source. The source support 34 can be made of a suitable neutron moderating material other than polyethylene but the neutron source 31 must be positioned at a predetermined distance away from the bottom of the extraction hole 32 so that neutrons emitted from the source are properly moderated as they emerge from the extraction hole. The neutron source 31 is also made accessible through a curved hole 33 instead of a straight hole as in the case of FIG. 2, so that the hole 33 does not have to be closed. The source is also adjustable in location along the curved hole by a flexible wire at one end of which the source is attached.

Figure 6:
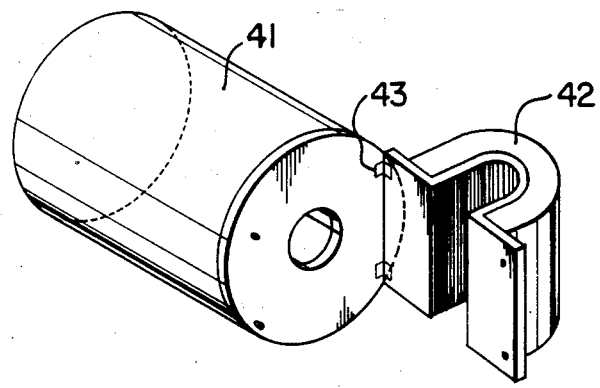
FIG. 6 shows a portable unit comprising the neutron beam extractor and the thermal neutron detector mount, mechanically attached to each other.

FIG. 6 shows a portable unit comprising the neutron beam extractor 41 and the thermal neutron detector mount 42, attached to each other by suitable mechanical means 43. The portable unit can be opened as shown in the figure to allow clamping of the unit on a pipe for use.

It has been a difficult problem to measure the steam quality of the high pressure wet steam by measuring the density because of the density change over a wide steam quality range is very small. For example, at a typical high pressure of 10 MPa, the density changes from 87.7 to 55.5 kg/m$^3$ when the quality changes from 0.6 to 1.0. This represents a very small density change of 0.8 kg/m$^3$ per 0.01 steam quality change.

Neutrons, and particularly thermal neutrons, are very sensitive to the presence of hydrogeneous material. This can be seen from the fact that the mean free path of thermal neutrons in water medium (H$_2$O) of 1000 kg/m$^3$ density is about 3 mm. Thus, the thermal/epithermal neutron transmission technique employed in the present invention is expected to be sensitive to the small density change of wet steam at high pressure over a wide range of steam quality. Indeed, from both theoretical calculations of the device according to the present invention, and results of experiments conducted with the device at our laboratories, it has been proven that the sensitivity of the present device is high enough to resolve a density change of 2 kg/m corresponding to a steam quality change of 0.025 for wet steam.

Thermal and epithermal neutrons required in the employed transmission technique are normally produced by a research nuclear reactor. This makes the techniques impractical. However, in the present invention, thermal and epithermal neutrons are produced from the moderation of neutrons emanating from a portable neutron source (all commercially available neutron sources emit neutrons of energies above thermal and epithermal range). The moderator (beam extractor) is not heavy. It weighs only about 30 kg. The whole unit is compact, robust, and portable. It is nonintrusive and does not disrupt the routine operations of the industrial processes.

We claim:

1. An apparatus for determining a property of high pressure wet steam in a metal pipe of a small cross-sectional area wherein the said property is related to the transmission characteristic of thermal/epithermal neutrons through the high pressure wet steam, comprising:
   a neutron beam extractor positioned near the exterior surface of the pipe to transmit a collimated beam of thermal/epithermal neutrons through the pipe, the said neutron beam extractor having a radioactive neutron source to emit neutrons of energies above thermal and epithermal range and source support means made of a neutron moderating material, the said source support means further having a chamber formed therein in which the radioactive neutron source is positioned and a straight collimating extraction hole of a small crosssection in the said neutron moderating material, the said extraction hole extending from the exterior surface of the source support means to near the chamber wherein the chamber and the extraction hole are spaced apart by a predetermined amount so that the fast neutrons emitted by the source will be moderated to become thermal/epithermal neutrons as they emerge into the extraction hole which will then collimate the thermal/epithermal neutrons into a beam, thermal neutron detector positioned near the exterior surface of the pipe on the side opposite to the neutron beam extractor to receive the thermal/epithermal neutrons transmitted through the pipe and to generate an output proportional thereto, and electronic counting means for processing the output of the thermal neutron detector to produce an indication of the property of the high pressure wet steam, the property being selected from a group consisting of the steam quality and the density.

2. The apparatus according to claim 1 wherein the neutron beam extractor and the thermal neutron detector are mechanically attached to each other to form a portable unit.

3. The apparatus according to claim 2 wherein the chamber is located at a first predetermined distance away from the wall of the extraction hole and at a second predetermined distance away from the bottom thereof.

4. The apparatus according to claim 3 wherein the chamber in the source support means is accessible through a source hole through which the source may be inserted into or removed from the chamber.

5. The apparatus according to claim 4 wherein the source hole is straight and a plug is provided to close the hole.

6. The apparatus according to claim 5 wherein the source hole is curved.

7. The apparatus according to claim 1 wherein the electronic counting means further comprise:

means for forming a signal representing the density $\rho$ of the high pressure wet steam from the output of the thermal neutron detector, and means for calculating from the signal to produce an indication of the steam quality x of the high pressure wet steam according to the following equations:

$$\rho = \rho_g \alpha + \rho_f(1 - \alpha) \quad (1)$$

$$\alpha = \frac{1}{1 + \frac{\rho_g}{\rho_f} \frac{U_g}{U_f} \frac{(1 - x)}{x}} \quad (2)$$

where $\rho_g$ and $U_g$=density and average velocity, respectively, of the steam phase of a steam-water mixture, $\rho_f$ and $U_f$=density and average velocity, respectively, of the water phase of a steam-water mixture, and $\alpha$=void fraction.

8. The apparatus according to claim 1 wherein the electronic counting means for processing the output comprises:

means for calibrating the said output proportional to the transmitted thermal/epithermal neutrons against known steam qualities of high pressure wet steam to derive an unknown steam quality.

9. The apparatus according to claim 8 wherein the neutron beam extractor and the thermal neutron detector are mechanically attached to each other to form a portable unit.

10. The apparatus according to claim 9 wherein the chamber is located at a first predetermined distance away from the wall of the extraction hole and at a second predetermined distance from the bottom thereof.

11. The apparatus according to claim 10 wherein the chamber in the source support means is accessible through a source hole through which the source may be inserted or removed from the chamber.

12. The apparatus according to claim 11 wherein the source hole is straight and a plug is provided to close the hole.

13. The apparatus according to claim 12 wherein the source hole is curved.

14. A method of determining a property of high pressure wet steam in a metal pipe of a small cross-sectional area, wherein the said property is related to the transmission characteristic of thermal/epithermal neutrons through the high pressure wet steam, comprising steps of:

generating neutrons of energies above thermal and epithermal range from a neutron source which is enclosed in a neutron moderating material, moderating the neutrons from the neutron source to thermal/epithermal neutrons by means of the said neutron moderating material, collimating the thermal/epithermal neutrons into a beam by means of a straight collimating extraction hole of a small cross section provided in the neutron moderating material, the said extraction hole extending from the exterior surface of the neutron moderating material to near the neutron source, transmitting the collimated beam of thermal/epithermal neutrons through a pipe, receiving by a thermal neutron detector the thermal/epithermal neutrons transmitted through the pipe to generate an output proportional thereto, and processing the output to produce an indication of the property of the high pressure wet steam, the said property being selected from a group consisting of the steam quality and the density.

15. The method according to claim 14 wherein the step of processing the output comprises steps of:

obtaining the density $\rho$ of the high pressure wet steam from the output proportional to the transmitted thermal/epithermal neutrons, and calculating, from the density $\rho$, the steam quality x of the high pressure wet steam according to the following equations:

$$\rho = \rho_g \alpha + \rho_f(1 - \alpha) \quad (1)$$

$$\alpha = \frac{1}{1 + \frac{\rho_g}{\rho_f} \frac{U_g}{U_f} \frac{(1 - x)}{x}} \quad (2)$$

where $\rho_g$ and $U_g$ = density and average velocity, respectively, of the steam phase of a steam-water mixture,
$\rho_f$ and $U_f$ = density and average velocity, respectively, of the water phase of a steam-water mixture, and
$\alpha$ = void fraction.

16. The method according to claim 15 further comprising a step of positioning the neutron source away from the side wall of the extraction hole to avoid line-of-sight paths of the $\gamma$-rays and fast neutrons to the thermal neutron detector through the extraction hole so that irradiation of the thermal neutron detector by $\gamma$-rays and fast neutrons from the neutron source is minimized.

17. The method according to claim 14 wherein the step of processing the output comprises:
a step of calibrating the said output proportional to the transmitted thermal/epithermal neutrons against known steam qualities of high pressure wet steam to derive an unknown steam quality.

* * * * *